United States Patent [19]

Metzner et al.

[11] Patent Number: 5,159,778

[45] Date of Patent: Nov. 3, 1992

[54] METHOD AND ARTICLE FOR THE PREVENTIVE PROTECTION OF MATERIALS AGAINST SOIL-DWELLING PESTS

[75] Inventors: Wolfgang Metzner, Krefeld; Michael Pallaske, Kempen; Hans-Werner Wegen, Krefeld, all of Fed. Rep. of Germany

[73] Assignee: Desowag Materialschutz GmbH, Duesseldorf, Fed. Rep. of Germany

[21] Appl. No.: 579,966

[22] Filed: Sep. 10, 1990

[30] Foreign Application Priority Data

Sep. 20, 1989 [DE] Fed. Rep. of Germany ....... 3931303

[51] Int. Cl.$^5$ ............................................. A01M 1/10
[52] U.S. Cl. ........................................ 43/121; 43/124; 43/107; 43/132.1; 52/101
[58] Field of Search ............... 43/121, 107, 124, 132.1; 424/409, 405

[56] References Cited

U.S. PATENT DOCUMENTS

| | | | |
|---|---|---|---|
| 2,857,630 | 10/1958 | Bishop | 43/132.1 x |
| 3,723,622 | 3/1973 | Büchel et al. | 514/383 |
| 3,969,439 | 7/1976 | Urbach et al. | 558/170 |
| 4,147,791 | 4/1979 | Meiser et al. | 514/383 |
| 4,233,293 | 11/1980 | Fuchs et al. | 514/93 |
| 4,389,530 | 6/1983 | Arlt et al. | 43/124 |
| 4,400,517 | 8/1983 | Gozzo et al. | 548/118 |
| 4,492,690 | 1/1985 | Boschi et al. | 514/94 |
| 4,563,344 | 1/1986 | Kotz et al. | 43/132.1 X |
| 4,823,520 | 4/1989 | Ebeling et al. | 52/101 |
| 4,965,254 | 10/1990 | Anderson et al. | 514/89 |
| 4,977,186 | 12/1990 | Gruening | 514/479 |
| 5,007,197 | 4/1991 | Barbett | 43/124 |
| 5,094,045 | 3/1992 | Tamashiro | 52/101 |

OTHER PUBLICATIONS

"Relation of Particle Size to the Penetration of Subterranean Termites through Barriers of Sand or Cinders," *Journal of Economic Entomology*, vol. 50, No. 5, pp. 690–692, Oct. 1957.

Primary Examiner—Richard K. Seidel
Assistant Examiner—Patty E. Hong
Attorney, Agent, or Firm—Foley & Lardner

[57] ABSTRACT

The invention relates to a method for the preventive protection of materials against pests permanently and/or temporarily living in the soil, in particular, termites. One or more barriers of sharp-edged inert particles of a particle size screened at from 0.001 to 30 mm and/or spherical inert particles having a diameter of 0.5 to 5.0 mm are arranged around and/or in the object to be protected.

21 Claims, 2 Drawing Sheets

METHOD AND ARTICLE FOR THE PREVENTIVE PROTECTION OF MATERIALS AGAINST SOIL-DWELLING PESTS

BACKGROUND OF THE INVENTION

The present invention relates to a method for the preventive protection of materials against pests permanently and/or temporarily living in the soil, in particular, termites.

In the tropics and subtropics, termites are among the economically most important wood destroyers. Nearly all wood-destroying termites belong to the lower termite species which have their nests in the soil. Starting from these nests, the animals burrow underground passages until they reach wood or another cellulose-containing material which is suitable as food. Termites, therefore, on the one hand, cause damage by feeding on wood used as a building material, and, on the other hand, they destroy a large number of other materials which get in the way during their search for suitable food. Termite damage typically is prevented by applying a termiticidal-active substance onto, or incorporating it into, the material to be protected.

It has proven difficult, however, to provide an effective termiticidal finish in the ground area of an object after that object has been used for building.

SUMMARY OF THE INVENTION

It is therefore an object of the present invention to provide a method for protecting articles against soil-dwelling pests, particularly termites. A further object of the present invention is to provide an article which is pest or termite-resistant, especially in areas of the article in or near soil.

In accomplishing the foregoing objects there is provided according to the present invention a method comprising arranging around the article at least one barrier comprised of at least one type of particle selected from the group consisting of sharp-edged inert particles having a particle size screened from about 0.001 to 30 mm, preferably from 0.5 to 1.15 mm, and spherical inert particles having a diameter of about 0.5 to 5.0 mm, preferably about 1.0 to 3.0 mm. The method may further comprise mixing the inert particles with a carrier material for an insecticidal, herbicidal and/or fungicidal-active substance to form the barrier material. Advantageously, the method also comprises applying an insecticidal, herbicidal and/or fungicidal active substance to the inert particles.

Another method according to the present invention comprises incorporating in the article at least one type of the above-described inert particles.

There also is provided according to the present invention an article having arranged on at least a part of its surface an inert particle barrier and/or incorporating the inert particles as an integral component.

Further objects, features and advantages of the present invention will become apparent from the detailed description of preferred embodiments that follows.

BRIEF DESCRIPTION OF THE DRAWINGS

The preferred exemplary embodiments of the present invention will hereinafter be described in conjunction with the following figures, wherein.

DETAILED DESCRIPTION OF THE PREFERRED EMBODIMENTS

Figure 1:
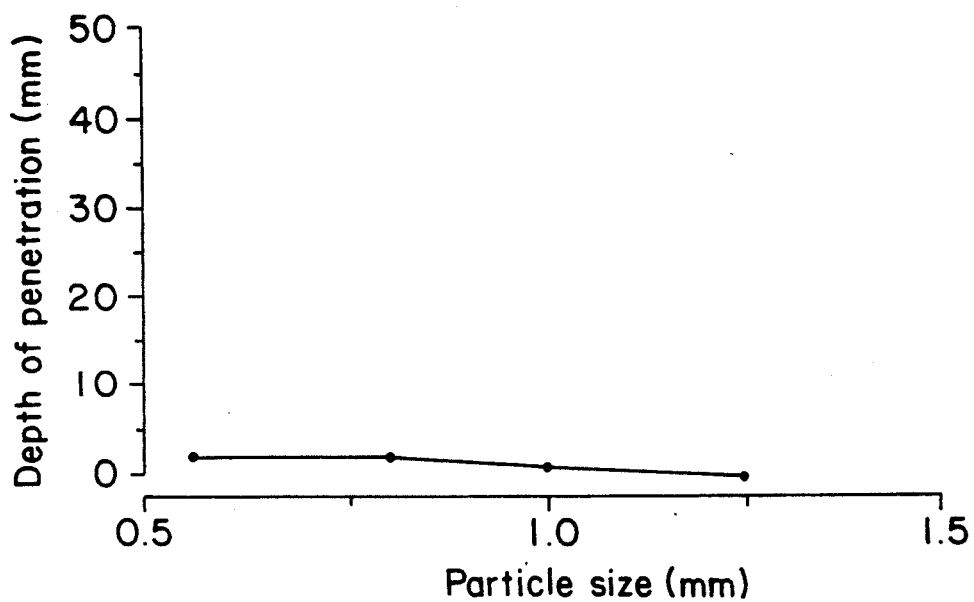
FIG. 1 is a graph representing the penetrability of a first embodiment of the present invention by termites of the species Reticulitermes santonensis.

According to the present invention one or more barriers of sharp-edged inert and/or spherical inert particles are arranged around and/or in the object to be protected. The barriers include sharp-edged inert particles having a particle size screened from about 0.001 to 30 mm (measured in accordance with DIN 4188), preferably from about 0.5 to 1.15 mm (measured in accordance with DIN 4188), and/or spherical inert particles having a diameter of about 0.5 to 5.0 mm, preferably of about 1.0 to 3.0 mm.

The method according to the present invention primarily utilizes the specific mechanical properties which preferentially prevail in a barrier of sharp-edged inert particles such as glass splinters. This bulk of particles has a high internal friction caused by the sharp particle edges, i.e., the individual particles are wedged together tightly, and therefore, can be removed from a structure only with difficulty by pests living in the soil, in particular, termites. The removal of individual particles is made even more difficult by the smooth surfaces of the individual particles. That is to say, the individual particles have a low static friction when seized. If the average particle size of the barrier material additionally is chosen so that the free spaces in the bulk of particles are smaller than the body diameter of the pests, then the barrier becomes impenetrable for these animals.

In a preferred embodiment of the method according to the present invention, one or more barriers of sharp-edged particles having a particle size screened from about 0.001 to 30 mm (measured in accordance with DIN 4188), preferably from about 0.5 to 1.15 mm (measured in accordance with DIN 4188), are arranged around and/or in the object to be protected.

In a particular embodiment, one or more barriers of spherical inert particles having bead diameters ranging from about 0.5 to 5.0 mm, preferably from about 1.0 to 3.0 mm, are arranged around and/or in the object to be protected.

In a further embodiment of the method according to the present invention, one or more barriers made of a mixture of sharp-edged inert particles having a particle size screened from about 0.56 to 1.5 mm (measured in accordance with DIN 4188) and spherical inert particles having a diameter of from about 0.56 to 3.0 mm are arranged around and/or in the object to be protected.

In a preferred embodiment, one or more barriers made of glass splinters, ground glass, glass tinsel or glass spangles as the sharp-edged inert particles and/or glass beads as the spherical inert particles are arranged around and/or in the object to be protected.

In an advantageous embodiment of the present invention, one or more barriers having a thickness of about 1 to 100 cm, preferably about 10 to 50 cm, of the sharp-edged and/or spherical inert particles are arranged around the object to the protected.

In another embodiment, one or more barriers of the sharp-edged and/or spherical inert particles are mixed with a carrier material for insecticidal, herbicidal and/or fungicidal-active substances and arranged around and/or in the object to be protected.

In a preferred embodiment of the present invention, the barriers of sharp-edged and/or spherical inert particles also serve as a carrier material for the application of insecticidal, herbicidal and/or fungicidal-active substances. The herbicidal and fungicidal active substances prevent damage to the barriers by the growth of roots or fungi.

It has proven advantageous for the sharp-edged and/or spherical inert particles to act as carrier material for an insecticidal-active pyrethroid, such as permethrin, fenfluthrin, decamethrin or cypermethrin, preferably, cyano-(4-fluoro-3-phenoxyphenyl)-methyl-3-(2,2-dichlorothenyl)-2,2-dimethylcyclopropanecarboxylate (cyfluthrin).

The pyrethroid can be partially or wholly replaced by other insecticidal-active substances, such as an insecticidal carbamate, for example, o-isopropoxyphenyl N-methyl-carbamate and/or o-secbutylphenyl N-methylcarbamate, an insecticidal phosphoric ester, phosphonic ester, thiophosphoric ester, dithiophosphoric ester or an insecticidal thionophosphoric ester, preferably, an insecticidal halogenated or halogen-free thionophosphoric ester represented by the formula

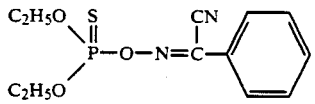

or O,O-diethyl O-(α-cyanobenzylidene-amino) thionophosphate and/or (diethoxythiophosphoryloximino)-2-chlorophenyl-acetonitrile and/or other phosphoric esters, preferably, dimethoxy-O-(6-nitro-m-tolyl)-phosphorothioate.

Fungicidal-active substances which can be applied to the carrier material include a 1-trityl-1,2,4-triazole represented- by the general formula

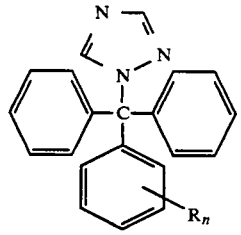

in which R represents a fluorine, chlorine or bromine atom, a trifluoromethyl, nitro or cyano group or an alkyl group having up to 4 carbon atoms, and n is 1 or 2, as well as their salts of organic or inorganic acids. The fungicidal-active substance can also be an (N-cyclohexyldiazeniumdioxy)metal compound or a salt of N-nitroso-N-cyclohexylhydroxylamine, preferably of an aluminum compound of these. Further useful fungicidal-active substances are 2,5-dimethyl-N-cyclohexyl-N-methoxy-3-furancarboxamide, N,N-dimethyl-N'-phenyl-N'-(fluorodichloromethylthio)sulfamide, N,N-dimethyl-N'-p-tolyl-N'-(dichlorofluoromethylthio)sulfamide, or a mixture of two or more of these compounds. In addition, tetravalent, fungicidal organotin compounds such as tributyltin benzoate, tris(tributyltin) phosphate, bis(tributyltin) oxide, tributyltin naphthenate, tributyltin octoate, as well as quaternary ammonium salts such as arylalkyl ammonium compounds, preferably a trialkylarylammonium compound such as benzyldimethyl $(C_{10}-C_{16})$alkylammonium chloride, can be utilized in the present invention.

The barriers according to the present invention are arranged in and/or on the soil around the object to be protected as well as in and/or on the object to be protected.

Application of the barrier to a building structure or other object can be effected in any manner capable of preventing soil-dwelling pests' access to the structure or object. This can be achieved for example by A.) homogenous barriers of splinter material, made by filling up areas and/or trenches adjacents of appropriate depth and width which are adjacent to the object to be protected.

B.) prefabricated sheets of splinter material embedded in an elastic carrier or binder material like (PVC, rubber, silicon-rubber etc.).

C.) coatings or sealings made of splinter material embedded in an elastic carrier or binder material like (PVC, rubber, silicon-rubber etc.).

The barrier also can be formed by applying any of the above-described mixtures to the structure or object to be protected prior to the placement of that structure or object in and/or on soil. This can be achieved by gapless or superimposed fixing of prefabricated sheets of splinter material (above-described method B) and/or application of barrier-layers (above-described method C) on and/or around the structure or object which has to be protected.

For example, a barrier can be formed below a building by spreading a homogenous, horizontal layer of splinter material below the fundament (above-described method A) avoiding accidental hardening of the barrier with subsequent rains by covering the layer with a waterproof foil before pouring the concrete fundaments. The same result can be achieved by gapless or superimposed spreading of prefabricated sheets of splinter material (above-described method B) and/or application of barrier-layers (above-described method C) below the fundaments.

The protection of existing- structures or objects can be achieved by digging a continuous trench adjacent around the object (approx. 5 to 10 cm width, approx. 75 to 150 cm depth) and then filling the trench with splinter material (above-described method A) or sealings (above-described method C). The same effect is achieved by gapless insertion of prefabricated sheets of splinter material (abovedescribed method B) into the trench.

The following results were obtained with respect to termites of the species Reticulitermes santonensis (de Feytaud) and Heterotermes indicola (Wasmann) when a preferred method according to the present invention with the sharp-edged glass particles as inert barrier material was applied:

A. Penetrability of Sharp-edged Barrier Material

A barrier can be penetrated by termites in two ways: first, by removal of particles and, second, by utilization of the hollow system between the particles. Penetration can only be prevented when, on the one hand, the particles are too large to be removed, but, on the other hand, small enough so that there is no passage between them for the termites.

The barriers were tested for penetration by termites in close conformity with DIN EN 117. The experimental set-up prescribed in this regulation was modified such that a glass tube, 70 mm in length (diameter 55 mm), was placed on the soil in the test container. This glass tube was packed with the barrier material to be tested (layer thickness 50 mm). On the barrier material there was placed a piece of wood which was highly attractive to termites (because of fungal infestation). The glass tube was then sealed at the top, the only way to the wood being through the layer.

The barrier of sharp-edged material has a high internal friction; the individual particles become tightly wedged and can only be removed from the composition with difficulty. To determine the effect of the internal friction on the penetrability of barriers by termites, barriers of glass splinters of various particle sizes were examined.

Figure 2:
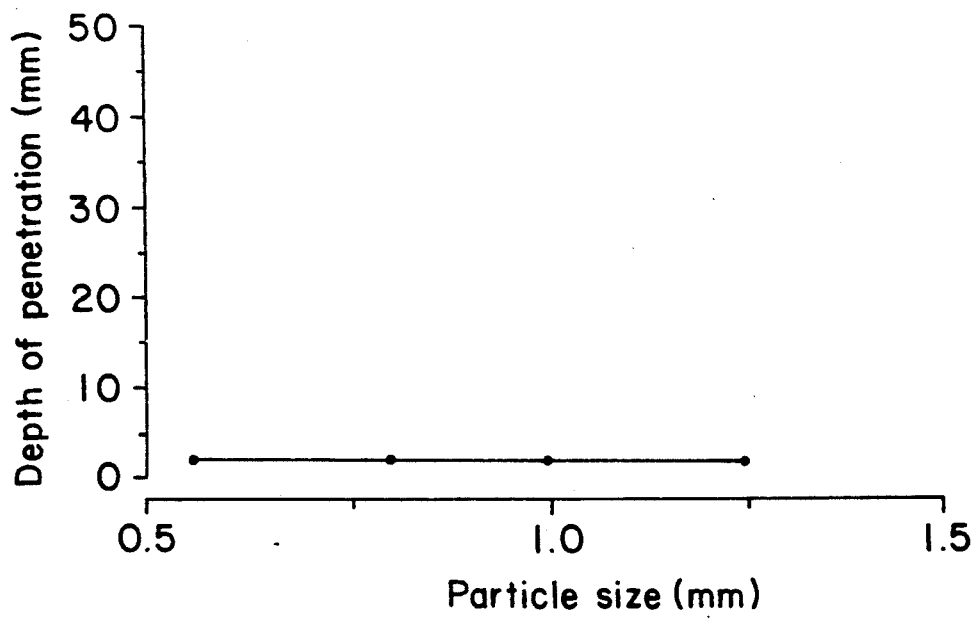
FIG. 2 is a graph representing the penetrability of the same first embodiment of the present invention by termites of the species Heterotermes indicola.

The high effectiveness of barriers of sharp-edged material is shown by FIGS. 1 and 2, which show the penetrability of barriers of glass splinters by termites of the species Reticulitermes santonensis (FIG. 1) and of the species Heterotermes indicola (FIG. 2) as a function of the particle size used (screening). Barriers of sharp-edged material up to a particle size of 0.56 mm are penetrated neither by Heterotermes indicola nor by Reticulitermes santonensis.

B. Penetrability of Rounded Barrier Material

Figure 3:
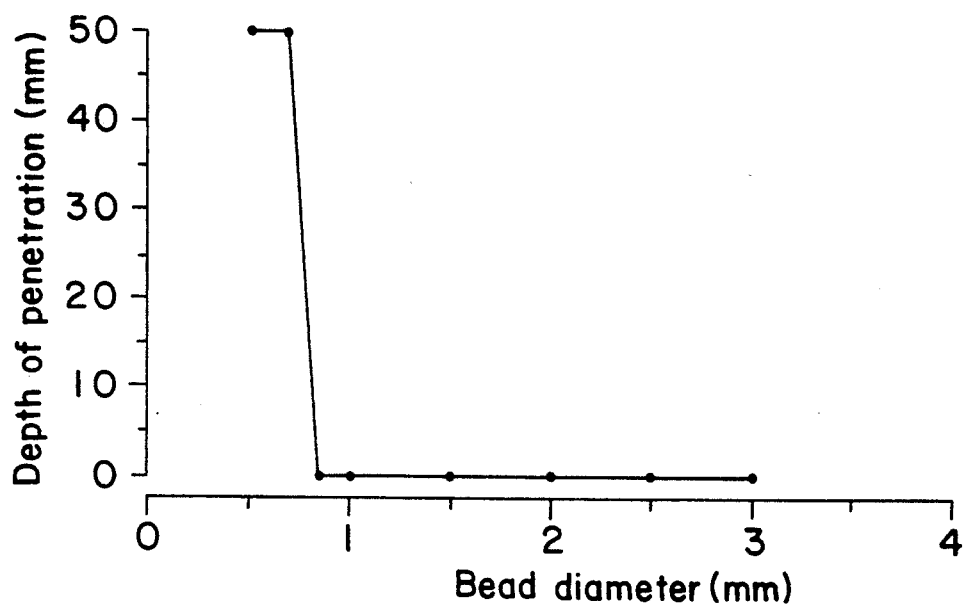
FIG. 3 is a graph representing the penetrability of a second embodiment of the present invention by termites of the species Reticulitermes santonensis.
Figure 4:
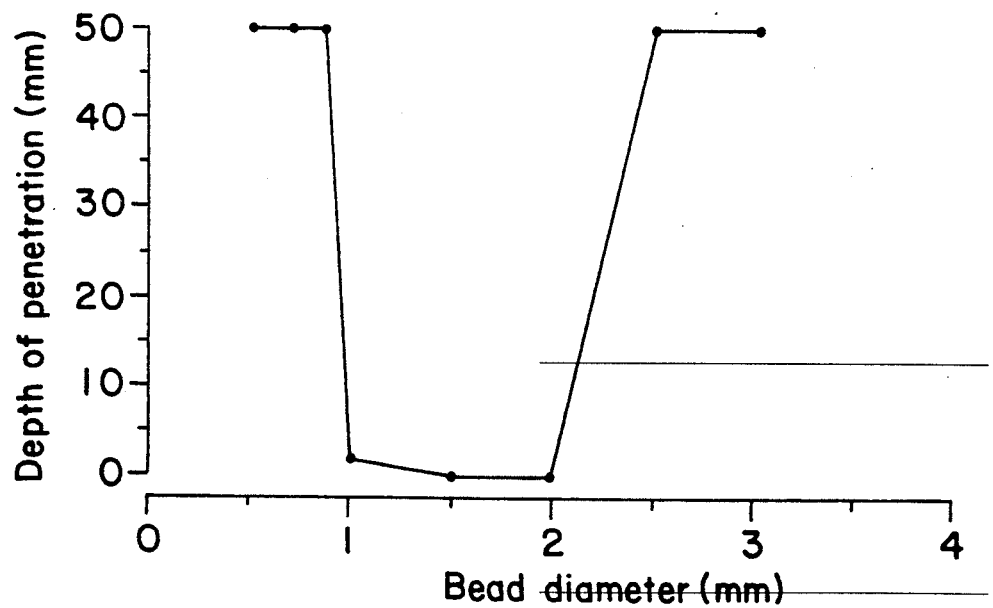
FIG. 4 is a graph representing the penetrability of the same second embodiment of the present invention by termites of the species Heterotermes indicola.

The test was carried out in accordance with the above-described modified DIN EN 117. The test results show that barrier material consisting of glass beads with bead diameters of 0.4 to 0.9 mm can be penetrated by removal; however, glass beads with diameters between 1.0 and 3.0 mm prevent penetration by termites (Reticulitermes santonensis) completely as shown in FIG. 3. Above a diameter of 2.5 mm, very small termite species (Heterotermes indicola) can find their way through the hollow system in the barrier material as shown in FIG. 4.

C. Penetrability of Mixed Barrier Material

The effects of mixtures of sharp-edged and spherical inert particles as barriers to termite penetrability also were investigated. The tests were carried out with layers of mixtures of spherical material (glass beads of diameter 0.56 to 3.0 mm) and sharp-edged material (glass splinters screened at from 0.56 to 1.5 mm) in accordance with the above-described modified DIN EN 117.

These tests showed that all mixtures were able to successfully prevent the penetration by Heterotermes indicola as well as Reticulitermes santonensis (depth of penetration into the barrier material: 2 mm maximum).

D. Penetrability of Barrier Material Treated with Insecticide

In a particular embodiment of the present invention, the barrier material is treated with an insecticidal-active substance. If glass is used as the barrier material, it is advantageous to use a synthetic pyrethroid as the insecticidal-active substance because of its high affinity to glass surfaces. The additional treatment of a barrier made of glass material with a synthetic pyrethroid proves advantageous both from an environmental point of view and with regard to the longevity of the insecticidal properties of this type of compound in the soil for the following reasons:

the active substance is no longer mixed directly with the soil and hence the risk of contaminating surface water is reduced greatly;

by virtue of the high affinity of the active substance to glass surfaces, its leaching, and hence pollution of the environment in general, is reduced drastically;

the neutral conditions in the interior of the barrier greatly extend the duration of activity of the pyrethroid, particularly in an alkaline environment;

the lack of organic material in the interior of the barrier greatly delays microbial degradation of the pyrethroid and further extends the duration of action of the latter.

Barriers which have been constructed in accordance with this particular embodiment, therefore, advantageously combine mechanical and chemical protection while simultaneously reducing pollution of the environment by termite control measures.

For this reason, the contact insecticidal activity of glass splinters (particle size screened from 0.56–1.15 mm), which briefly had been immersed in a solution which included a pyrethroid (0.1% of cyfluthrin in acetone), was tested. 24 hours after immersion (complete evaporation of the solvent), batches of 50 termites were placed on the layer of glass splinters and the mortality was determined every 30 minutes.

| | |
|---|---|
| Batch I | Immersion time 2 minutes |
| Batch II | Immersion time 3 minutes |
| Batch III | Immersion time 4 minutes |
| Test animal | *Heterotermes indicola* |
| Examination 24 hours after immersion: | |
| Batch I | 100% mortality after less than 30 minutes |
| Batch II | 100% mortality after less than 30 minutes |
| Batch III | 100% mortality after less than 30 minutes |
| Examination after leaching conditions (7 days under water, one complete change of water per day): | |
| Batch I | 100% mortality after less than 30 minutes |
| Batch II | 100% mortality after less than 30 minutes |
| Batch III | 100% mortality after less than 30 minutes |
| Test animal | *Reticulitermes santonensis* |
| Examination 24 hours after immersion: | |
| Batch I | 100% mortality after less than 30 minutes |
| Batch II | 100% mortality after less than 30 minutes |
| Batch III | 100% mortality after less than 30 minutes |
| Examination after leaching conditions (7 days under water, one complete change of water per day): | |
| Batch I | 100% mortality after less than 30 minutes |
| Batch II | 100% mortality after less than 30 minutes |
| Batch III | 100% mortality after less than 30 minutes |

These results show that barrier material of glass, preferably in the form of sharp-edged glass material, can be used advantageously as a carrier substance for termiticidal-active substances, particularly those substances selected from the group of synthetic pyrethroids.

E. Penetrability of Barrier Material Made of a Mixture of Sharp-edged Inert Particles and a Carrier Material Tests were carried out using a cable insulating material made of soft polyvinyl chloride which is not resistant to termites. The glass particles used as the inert particles are mixed with the molten soft polyvinyl chloride which acts as the carrier material, in various ratios by volume, and the mixture is allowed to cool. The test material is made into disks of 2 mm thickness and tested in accordance with DIN EN 117, modified as described above.

| | |
|---|---|
| Batch I | Glass splinters (particle size 0.56–1.15 mm) |
| Batch II | Glass spangles (particle size 0.8 mm) |
| Batch III | Glass spangels (particle size 0.42 mm) |

Mixing ratio in parts by volume of particles/parts by volume of soft PVC

| | Mixture | Evaluation of feeding |
|---|---|---|
| Test animals: *Heterotermes indicola* | | |
| Batch I | 80/20 | superficial rasping 0.5 mm |
| | 50/50 | superficial rasping 0.5 mm |
| Batch II | 80/20 | superficial rasping 0.5 mm |
| | 50/50 | superficial rasping 0.5 mm |
| | 20/80 | superficial rasping 0.5 mm |
| Batch III | 80/20 | superficial rasping 0.5 mm |
| | 50/50 | superficial rasping 0.5 mm |
| | 20/80 | superficial rasping 0.5 mm |
| Test animal: *Reticulitermes santonensis* | | |
| Batch I | 80/20 | superficial rasping 0.5 mm |
| | 50/50 | superficial rasping 0.5 mm |
| | 20/80 | superficial rasping 0.5 mm |
| Batch II | 80/20 | superficial rasping 0.5 mm |
| | 50/50 | superficial rasping 0.5 mm |
| | 20/80 | superficial rasping 0.5 mm |
| Batch III | 80/20 | superficial rasping 0.5 mm |
| | 50/50 | superficial rasping 0.5 mm |
| | 20/80 | superficial rasping 0.5 mm |

These results show that soft polyvinyl chloride, which is not resistant to termites, can be made termite-resistant by the incorporation of a barrier of glass particles according to the present invention. The present invention, therefore, is useful as a preventive protection against solid-dwelling pests for underground leads or cables, by arranging it around these leads or cables as a separate barrier material for coatings or by forming these leads or cables so that a barrier material is an integral component of the lead or cable material itself.

What is claimed is:

1. A method for the protection of an object against soil-dwelling pests, comprising arranging around the object at least one barrier comprised of a mixture of sharp-edged inert particles having a particle size screened from about 0.001 to 30 mm and spherical inert particles having a diameter of about 0.5 to 5.0 mm, wherein the sharp-edged and spherical inert particles are selected from the group consisting of glass splinters, ground glass, glass tinsel, glass spangles and glass beads.

2. A method according to claim 1, wherein the sharp-edged inert particles have a particle size screened from about 0.5 to 1.15 mm.

3. A method according to claim 1, wherein the spherical inert particles have a diameter of about 1.0 to 3.0 mm.

4. A method according to claim 1, wherein the barrier comprises a mixture of sharp-edged inert particles having a particle size screened from about 0.56 to 1.5 mm and spherical inert particles having a diameter of about 0.56 to 3.0 mm.

5. A method according to claim 1, wherein the barrier has a thickness of about 1 to 100 cm.

6. A method according to claim 1, wherein the barrier has a thickness of about 10 to 50 cm.

7. A method according to claim 1, further comprising mixing the sharp-edged and spherical inert particles with a carrier material for an insecticidal, herbicidal or fungicidal-active substance to form the barrier material.

8. A method according to claim 1, further comprising applying an insecticidal, herbicidal or fungicidal-active substance to the sharp-edged and spherical inert particles.

9. A method according to claim 8, wherein the fungicidal-active substance is selected from the group consisting of an (N-cyclohexyldiazeniumdioxy) metal compound, a salt of N-nitroso-N-cyclohexylhydroxylamine, 2,5-dimethyl-N-cyclohexyl-N-methoxy-3-furancarboxamide, N,N-dimethyl-N'-phenyl-N'-(fluorodichloromethylthio)sulfamide, N,N-dimethyl-N'-p-tolyl-N'-(dichlorofluoromethylthio)sulfamide, tributyltin benzoate, tris(tributyltin) phosphate, bis(tributyltin) oxide, tributyltin naphthenate, tributyltin octoate, a trialkylarylammonium compound and a 1-trityl-1,2,4-triazole compound represented by the general formula

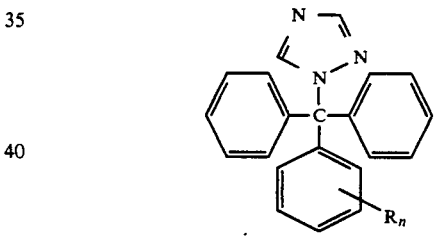

in which R represents a fluorine, chlorine or bromine atoms, a trifluoromethyl, nitro or cyano group or an alkyl group having up to 4 carbon atoms, and n is 1 or 2.

10. A method according to claim 9, comprising applying at least one insecticidal pyrethroid to the sharp-edged or spherical inert particles.

11. A method according to claim 10, wherein the pyrethroid is selected from the group consisting of permethrin, fenfluthrin, decamethrin, cypermethrin and cyano-(4-fluoro-3-phenoxyphenyl)-methyl-3-(2,2-dichlorothenyl)-2,2-dimethylcyclopropanecarboxylate.

12. A method according to claim 10, further comprising applying at least one other insecticidal-active substance in addition to the pyrethroid.

13. A method according to claim 12, wherein the other insecticidal-active substance is selected from the group consisting of an insecticidal carbamate, phosphoric ester, phosphonic ester, thiophosphoric ester, dithiophosphoric ester and thionophosphoric ester.

14. A method according to claim 1, wherein the barrier is formed by providing a void in the soil arranged around the object and then filling the void with the inert particles.

15. A method according to claim 1, wherein the barrier comprises a prefabricated sheet which includes the inert particles embedded in a binder material.

16. A method according to claim 1, wherein the barrier is formed by applying to the object a coating comprising the inert particles and a binder material.

17. A method according to claim 1, wherein said soil-dwelling pests comprise termites.

18. A method for the protection of an object against soil-dwelling pests, comprising admixing with the object at least one type of particle selected from the group consisting of sharp-edged inert particles having a particle size screened from about 0.001 to 30 mm and spherical inert particles having a diameter of about 0.5 to 5.0 mm, wherein the sharp-edged and spherical inert particles comprise particles selected from the group consisting of glass splinters, ground glass, glass tinsel, glass spangles and glass beads.

19. A method according to claim 18, wherein the sharp-edged inert particles have a particle size screened from about 0.5 to 1.15 mm.

20. A method according to claim 18, wherein the spherical inert particles have a diameter of about 1.0 to 3.0 mm.

21. A method according to claim 18, wherein said soil-dwelling pests comprise termites.

* * * * *